(12) United States Patent
Aharoni

(10) Patent No.: US 7,101,397 B2
(45) Date of Patent: Sep. 5, 2006

(54) IOL IMPLANTATION

(76) Inventor: Eli Aharoni, 4A Kehilat Venezia Street, Neot Afeka, Tel Aviv 69400 (IL)

(*) Notice: Subject to any disclaimer, the term of this patent is extended or adjusted under 35 U.S.C. 154(b) by 14 days.

(21) Appl. No.: 10/638,396

(22) Filed: Aug. 12, 2003

(65) Prior Publication Data

US 2004/0034414 A1    Feb. 19, 2004

Related U.S. Application Data

(60) Provisional application No. 60/403,432, filed on Aug. 15, 2002.

(51) Int. Cl.
*A61F 2/16*    (2006.01)
*A61F 9/013*    (2006.01)

(52) U.S. Cl. .................... 623/6.34; 623/6.41; 606/107

(58) Field of Classification Search ................ 606/107; 623/5.13, 6.11, 6.12, 6.14, 6.32, 6.34, 6.39, 623/6.41, 907

See application file for complete search history.

(56) References Cited

U.S. PATENT DOCUMENTS

| 5,628,798 | A | * | 5/1997 | Eggleston et al. | ......... | 623/6.11 |
| 5,814,103 | A | * | 9/1998 | Lipshitz et al. | ............ | 623/6.34 |
| 5,876,442 | A | * | 3/1999 | Lipshitz et al. | ............ | 623/6.34 |
| 6,277,146 | B1 | * | 8/2001 | Peyman et al. | ............ | 623/6.17 |

FOREIGN PATENT DOCUMENTS

EP    897702 A2 *  2/1999

* cited by examiner

*Primary Examiner*—David H. Willse
*Assistant Examiner*—Javier G. Blanco
(74) *Attorney, Agent, or Firm*—Dekel Patent Ltd.; David Klein

(57) ABSTRACT

A method for implanting a new intraocular lens (IOL) in an eye without removing the existing IOL, comprising forming a mounting hole in an IOL already implanted in an eye, and mounting another IOL in the mounting hole. Apparatus is also disclosed including a first IOL formed with a mounting hole, and a second IOL mounted in the mounting hole.

1 Claim, 2 Drawing Sheets

IOL IMPLANTATION

This application claims the benefit of Provisional App. No. 60/403,432, filed Aug. 15, 2002.

FIELD OF THE INVENTION

The present invention relates generally to intraocular lens (IOL) implants and particularly to a method of implanting a new IOL in an eye without removing the existing IOL.

BACKGROUND OF THE INVENTION

Intraocular lens (IOL) implants generally are implanted in the capsular bag and held in place by haptics. The haptics may be wires or plate haptics. With time, fibrous tissue may form around the haptics, further anchoring the IOL in place.

An IOL may be implanted in a human eye during cataract surgery as a replacement for the opacified natural lens. IOLs have also been developed for other eye diseases or disorders, such as macular degeneration. For example, U.S. Pat. Nos. 5,354,335; 5,391,202; 5,814,103; 5,876,422; 5,928,283; 6,007,579; and 6,066,171, all assigned to Visioncare Ltd., Yehud, Israel, the disclosures of which are incorporated herein by reference, describe telescopic IOLs. The telescopic intraocular inserts may comprise a positive (converging) lens facing the anterior side of the eye and a negative (diverging) lens facing the posterior side, the two lenses forming a Galilean telescopic system. Alternatively, the inserts may comprise a reverse Galilean telescopic system.

Sometimes it may be desirable to remove an IOL already implanted in the eye, and replace it with another IOL. For example, patients, who already have a regular IOL implanted in the eye, may develop macular degeneration. In such a case, it would be desirable to remove the existing IOL and replace it with a telescopic IOL. However, the anchoring of the haptic with fibrous tissue may make it very difficult or impossible to remove the first IOL without tearing or causing damage to adjacent tissues in the eye.

SUMMARY OF THE INVENTION

The present invention seeks to provide a method for implanting a new IOL (the term IOL being used throughout the specification and claims to encompass any kind of device implantable in an eye, such as but not limit to, optical, mechanical or electronic devices) in an eye without removing the existing IOL. For example, the invention may be used for implanting a telescopic IOL without removing the existing IOL, as described hereinbelow.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
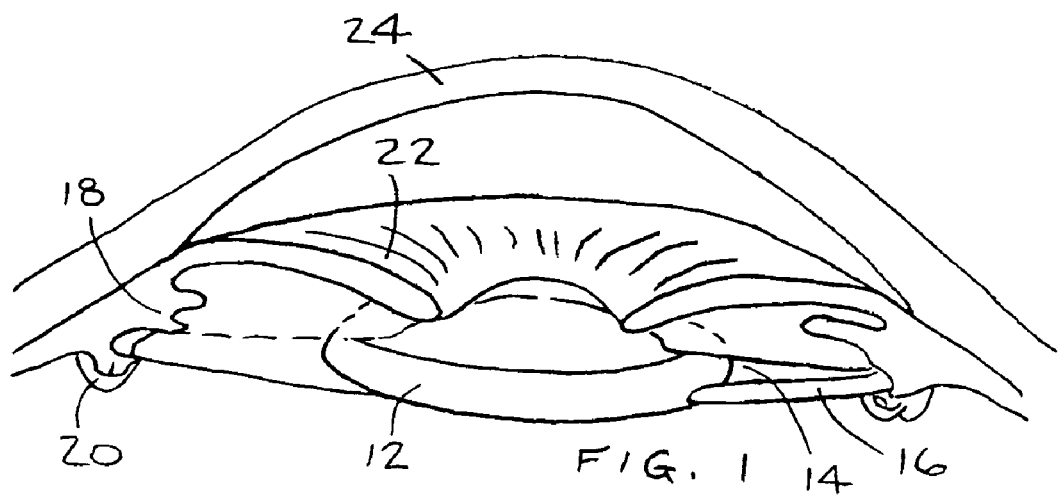
FIG. 1 is a simplified pictorial illustration of an intraocular lens (IOL) implant implanted in an eye.
Figure 2:
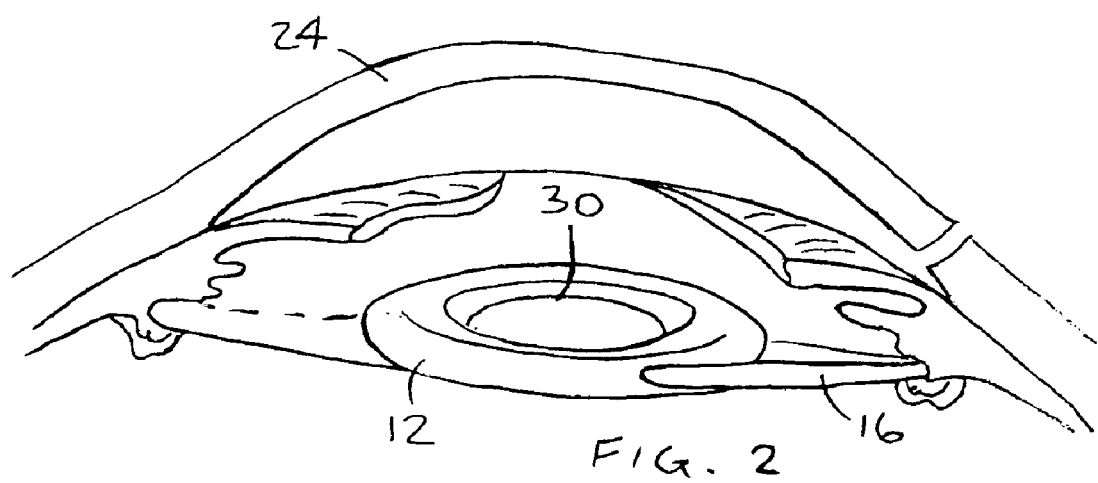
FIG. 2 is a simplified pictorial illustration of forming a mounting hole in the IOL implant, in accordance with a preferred embodiment of the present invention.
Figure 3:
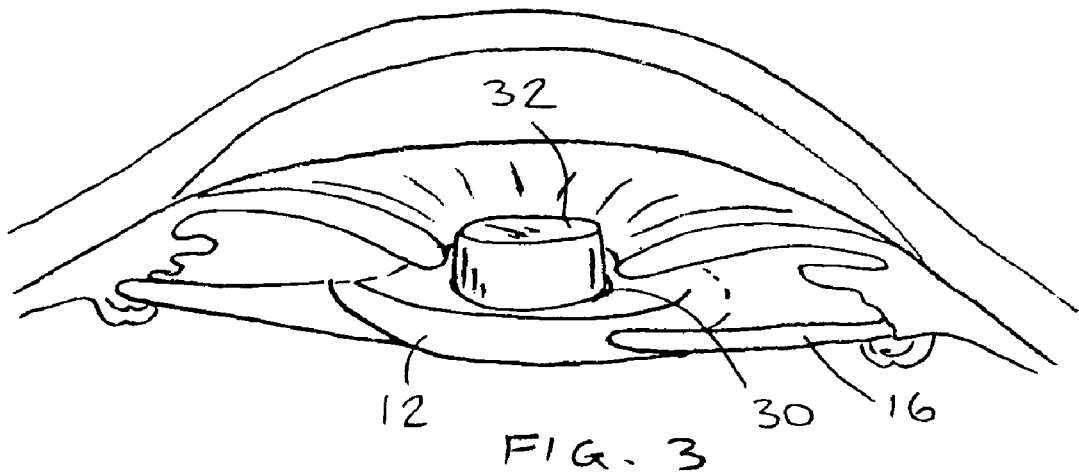
FIG. 3 is a simplified pictorial illustration of mounting another IOL implant, such as but not limited to a telescopic IOL implant, in the mounting hole formed in the first IOL, in accordance with a preferred embodiment of the present invention.
Figure 4:
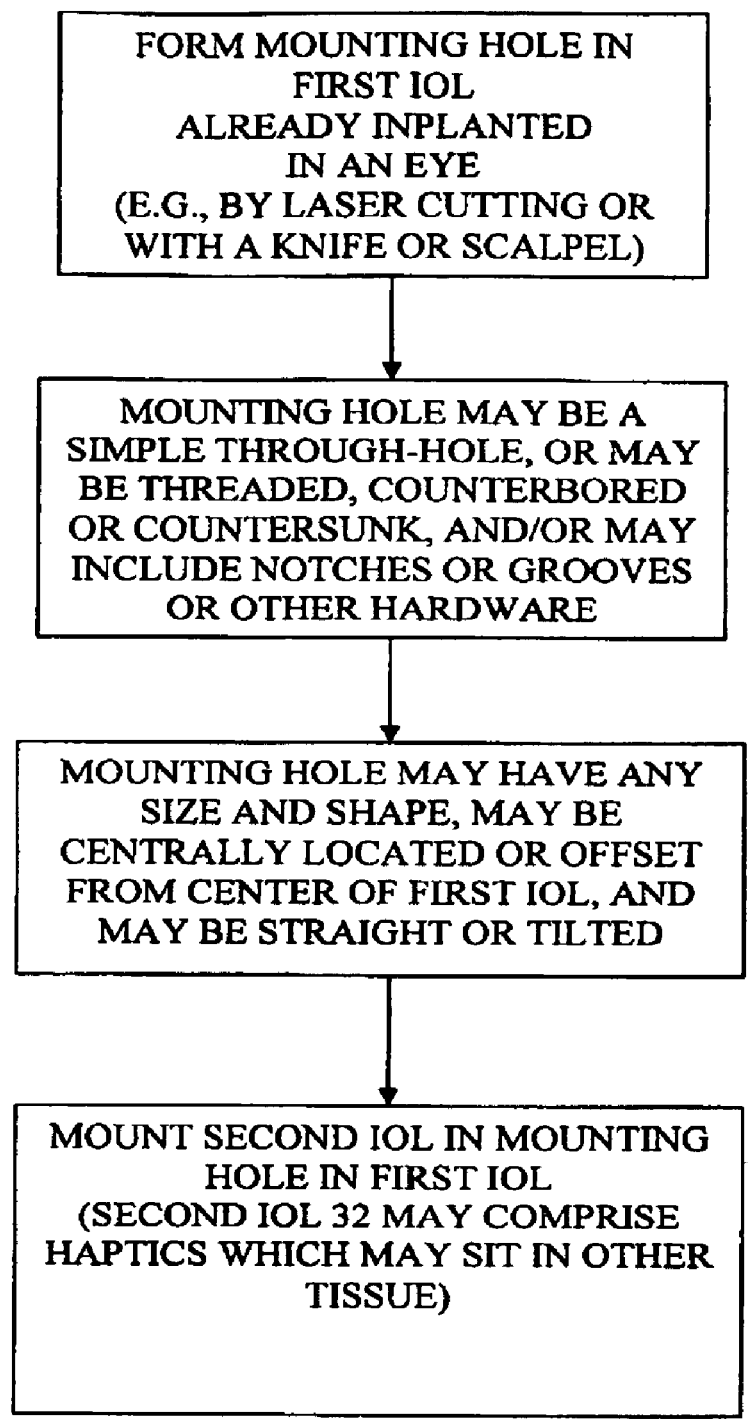
FIG. 4 is a simplified flow chart of mounting another IOL implant in the mounting hole formed in the first IOL, in accordance with a preferred embodiment of the present invention.

Reference is now made to FIGS. 1–3, which illustrate a method for implanting a new IOL in an eye without removing the existing IOL, in accordance with a preferred embodiment of the present invention.

FIG. 1 illustrates an intraocular lens (IOL) 12 implanted in the capsular bag 14. One or more haptics 16 fix the IOL to eye structure, such as the ciliary processes 18 and the zonules 20. FIG. 1 also illustrates other structures of the eye, such as the iris 22 and the cornea 24.

In FIG. 2, a mounting hole 30 may be formed in IOL 12. Mounting hole 30 may be formed by any convenient method, such as but not limited to, laser cutting or with a knife or scalpel. Mounting hole 30 may be a simple through-hole, or may be threaded, counterbored or countersunk, and/or may include notches or grooves or other hardware, fasteners or other suitable structure for mounting thereat another IOL. The capsular bag 14 may also be cut if necessary.

In FIG. 3, a second IOL 32 is mounted in mounting hole 30. The second IOL 32 may be constructed of any clear, transparent, biologically compatible material, such as but not limited to, polymethylmethacrylate (PMMA), silicone, silicone rubber, collagen, hydrogel, hyaluronic acid (including the sodium, potassium and other salts thereof), polysulfones, thermolabile materials and other relatively hard or relatively soft and flexible biologically inert optical materials.

The second IOL 32 may comprise any kind of IOL, such as but not limited to, single or multi-lens IOLs, or telescopic IOLs (e.g., Galilean or reverse Galilean telescope). The second IOL 32 may be without haptics. Alternatively, the second IOL 32 may comprise haptics which may sit in other tissue, such as in the sulcus, for example.

The mounting hole 30 may have any size and shape, may be centrally located or offset from the center of the first IOL 12, and may be straight or tilted, for example.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A method for implanting a second intraocular lens (IOL) in an eye without removing a first IOL already implanted in the eye, comprising:

forming a mounting hole in situ in a first non-telescopic IOL already implanted in an eye; and mounting a second non-telesconic IOL in situ in the mounting hole.

* * * * *